(12) United States Patent
Pace

(10) Patent No.: US 6,464,668 B1
(45) Date of Patent: Oct. 15, 2002

(54) NASOGASTRIC TUBE STABILIZER

(76) Inventor: Patrick Pace, 1945 Thomson Rd., Charlottesville, VA (US) 22903

(*) Notice: Subject to any disclaimer, the term of this patent is extended or adjusted under 35 U.S.C. 154(b) by 97 days.

(21) Appl. No.: 09/666,233

(22) Filed: Sep. 21, 2000

Related U.S. Application Data

(60) Provisional application No. 60/154,926, filed on Sep. 21, 1999.

(51) Int. Cl.$^7$ .................................................. A61M 5/32
(52) U.S. Cl. ...................................................... 604/179
(58) Field of Search ........................ 604/516, 79, 94.01, 604/171, 174–5, 177, 179, 524, 539, 910

(56) References Cited

U.S. PATENT DOCUMENTS

| | | | |
|---|---|---|---|
| 4,634,425 A | | 1/1987 | Meer ............................ 604/54 |
| 4,778,448 A | | 10/1988 | Meer ............................ 604/54 |
| 5,185,005 A | * | 2/1993 | Ballantyne ............. 128/207.18 |
| 5,913,852 A | * | 6/1999 | Magram ...................... 604/284 |

\* cited by examiner

*Primary Examiner*—Michael J. Hayes
*Assistant Examiner*—Michelle Lewis
(74) *Attorney, Agent, or Firm*—Sheldon H. Parker

(57) ABSTRACT

The disclosed appliance enables the rapid insertion of a tube around the nasal septum of a patient to form a harness onto which to secure a medical tube entering through the nasal passage. The appliance has a feed through arm having a first end angled to form a first handle member. A receiving arm, having a first end angled to form a second handle member and is attached to the feed arm by a swivel juncture. A fulcrum housing at the proximal end of the upper clamping member forms a swivel juncture to enable a lower clamping member, extending from the fulcrum housing to the second end of the receiving arm second end, to be moveable. The feed arm and receiving arm move in a scissor like manner on a first plane while the upper and lower clamping members move on a second plane, angled to the first plane.

18 Claims, 4 Drawing Sheets

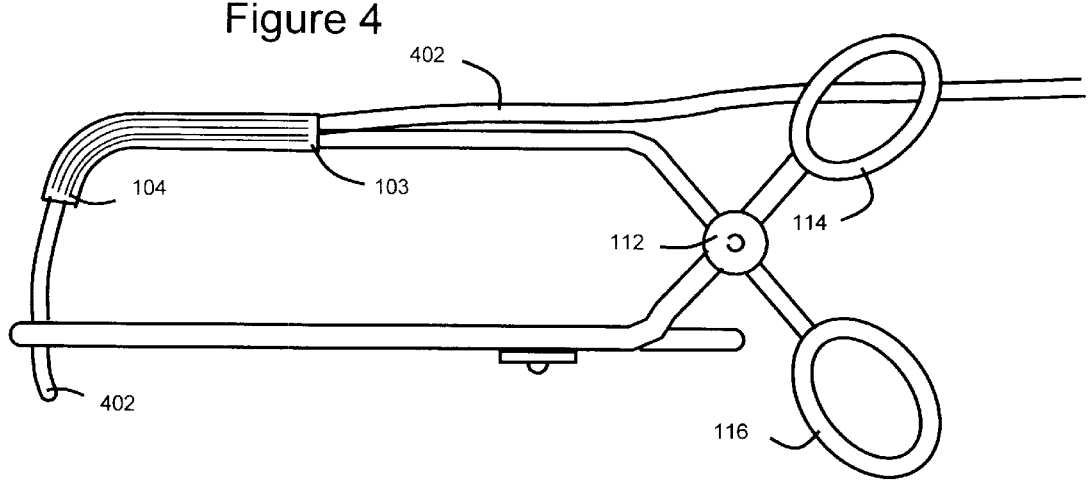

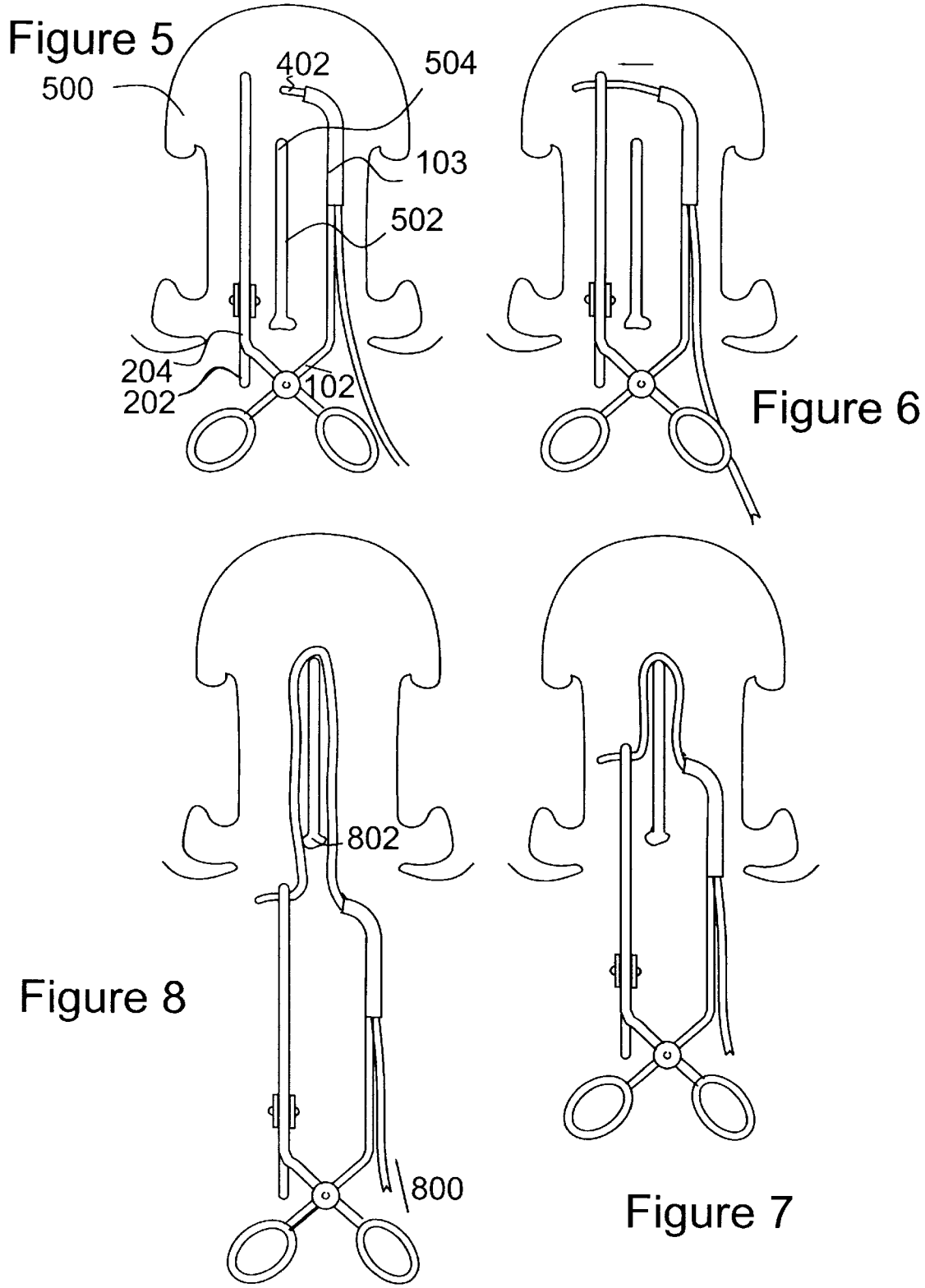

NASOGASTRIC TUBE STABILIZER

CROSS-REFERENCE TO RELATED PATENT APPLICATION

The present application claims the benefits under 35 U.S.C. 119(e) of provisional patent application Ser. No. 60/154,926, filed Sep. 21, 1999. This application incorporates by reference, as though recited in full, the disclosure of copending provisional application 60/154,926.

FIELD OF THE INVENTION

This invention relates to a method and apparatus for securing nasal tubes to patients, and more particularly, to a device for use in the securing of a nasogastric or nasoenteral tube to a patient.

BACKGROUND OF THE INVENTION

Nasal tubes, also known as nasoenteral, nasogastric, nasoduodenal, stomach tubes, or feeding tubes, collectively referred to as nasogastric tubes, are used commonly in the course of patient health care, most frequently in preparation for, during, and after surgery. The nasogastric tube has been a problem for patients and clinicians for some time. Patients, especially when agitated, have been known to pull out nasogastric tubes because they can be so uncomfortable. This creates a problem for both the patient and the clinicians because it is necessary to have a new nasogastric tube inserted for each on that is prematurely pulled out by the patient. The repeated insertion of nasogastric tube exacerbates the suffering of the patient and results in time being wasted by the clinician reinserting the tube.

These tubes typically are formed from a resilient plastic material such as polyurethane, polyethylene, or a silicone polymer. Typically, the tube has a proximal end, a distal end and a central lumen or passageway. Further details about nasogastric tubes can be found in U.S. Pat. No. 4,778,448 and 4,634,425, the disclosures of which are incorporated herein by reference, as though recited in full.

Various techniques have been developed for securing a nasogastric tube to the patient to prevent accidental or premature removal of the tube. Such techniques include using adhesive tape to secure the tube to the patient, using an adjustable or flexible tube holder for retaining the tube placed adjacent the nostril opening and secured to the patient by a harness going around the patient's head, and a tube holder that has a self-attached hook means that holds a nose piece that holds a nosepiece onto the nose. The problem with the aforementioned external harnesses is that they are clumsy, can be removed easily, for example, by an uncooperative patient, and can be easily dislodged accidentally, for example, during restless sleep. Further details about these and other prior art examples can be found in U. S. Pat. No. 4,778,448.

A further attempt to secure the tube to the patient has involved suturing the tube to the patient's tissue, most commonly the nasal columella. The problems with such stitching are that chronic pulling on the tube and constant nasal secretions can result in local infection and significant damage to the nasal columella, including, of example, sawing the columella in two.

U.S. Pat. No. 4,778,448 illustrates a method for anchoring or securing tubes in a nostril of a patient, particularly nasoenteral tubes for use in nutrient solution feeding or gastric fluid drainage. The '448 structure includes a harness for securing a tube to a patient, a nasoenteral tube, and means for securing the harness to the nasoenteral tube along the length of the tube. The harness comprises an elongated body having a first end disposed toward the distal end of the tube and a second end disposed toward the proximal end of the tube. The first end is adapted to be passed through the nostril (nasal choana), preferably simultaneously with insertion of the nasoenteral tube in a first nostril. The second end of the harness is adapted to be inserted into the second nostril and connected to the first end so that the first and second ends may be secured together to form a loop passing through both nostrils that can be adjusted to fit closely about the nasal columella and the posterior aspect of the nasal septum. The procedure is illustrated in FIGS. 2A through 2M. The end result is illustrated in FIG. 2N with an alternate shown in FIG. 2O. The system of the '448 patent produces a desirable end result, but is a long, complicated, tedious procedure.

SUMMARY OF THE INVENTION

The disclosed appliance enables the rapid insertion of a tube around the nasal septum of a patient to form a harness to support a medical tube. The appliance has a feed through arm having a first end angled to form a first handle member and a second end consisting of a hollow, tubular guide member having an approximately 90 degree curve at the distal end. A receiving arm, having. a first end angled to form a second handle member, forms a second member. A handle pivot forms a swivel juncture between the receiving arm and feed through arm to enable the receiving arm handle and the feed through arm handle to move relative to one another in a scissor action along a first plane.

An upper clamping member is formed from a portion of the receiving arm length. A fulcrum housing at the proximal end of the upper clamping member forms a swivel juncture to enable a lower clamping member, extending from the fulcrum housing to the second end of the receiving arm second end, to be moveable. The lower clamping member moves, in relation to the upper clamping member, along a second plane. Preferably both the upper and lower clamping members have gripping members along their adjacent surfaces.

A spring member within the housing biases the lower clamping member adjacent the upper clamping member. The lower clamping member is moved, relative to the upper clamping member, by a handle member affixed to the lower clamping arm.

The movement of the handles causes the feed through arm and receiving arm to move relative to one another on a first plane while movement of the handle member causes the upper clamping member and said lower clamping member to move relative to one another on a second plane.

The feed through arm/tubular guide member and the receiving arm have a length sufficient to place the distal end of the tubular guide member and second end of the receiving arm second end past the nasal septum. Once in position, the curved distal end of the tubular guide member directs a tube behind the nasal septum to be received by the receiving arm, where the tube is gripped by the upper and lower clamping members. The tube is maintained between the upper and lower clamping members during withdrawal of the appliance. Once withdrawn, the tube is secured below a patient's columella, such as by tying the ends together with a medically approved material.

Alternatively, the tube can be secured with a retaining device having a first end and a second end and multiple slots, each of the slots extending from the first end to the second end. At least two of the slots are dimensioned to retain the tube harness and at least a third of the slots is dimensioned to receive medical tubing. Thus, the harness serves as a securing point for a medical tube inserted into a patient's body through a nasal passage.

To form the harness by inserting the tube around the nasal septum of a patient, the tubular guide is inserted into a first nasal passage of a patient. The end of the tube is fed through the tubular guide and directed through an open end of the tubular guide and around the nasal septum. The first end of the tube is clamped, and held, by the receiving arm in the second nasal passage. The tube is then fed through the nasal passages as the appliance is withdrawn. The ends of the tube are then secured to one another to form the harness to enable the attachment of a medical tube that enters the patient's body through the nasal passages.

BRIEF DESCRIPTION OF THE DRAWINGS

The advantages of the instant disclosure will become more apparent when read with the specification and the drawings, wherein:

FIG. 4 is a top view of the applicator device showing the feeding tube fed through the tubular guide and having its distal end held by the clamp;

FIG. 5 is schematic plan view of the applicator positioned in the nasal passages;

FIG. 6 is a schematic plan view of the applicator positioned in the nasal passages showing the feeding tube fed through the tubular guide and having its distal end held by the clamp;

FIG. 7 shows the feeding tube fed through the tubular guide and providing sufficient slack to permit the applicator to be withdrawn;

FIG. 8 shows the applicator complete withdrawn from the nasal passages with the feeding tube in position to be trim and clamped;

DESCRIPTION OF THE PREFERRED EMBODIMENTS OF THE INVENTION

It has now been found that the problem of the prior art systems can be overcome through the use of a tool that transforms the procedure disclosed in U.S. Pat. No. 4,778, 448 into a rapid, simple, reliable operation. The tool consists of a scissor-like fulcrum having two sets of elongated arms and corresponding handles. One set of the elongated arms is a pair of cooperating scissor-like fulcrum arms that serve as a clamping mechanism. Preferably, the clamping arms are spring biased to the closed position. The other set of the elongated arms is an elongated arm and a tubular, tube guide member. Each of the two sets of elongated arms is designed to fit into a nasal passage.

Figure 1:
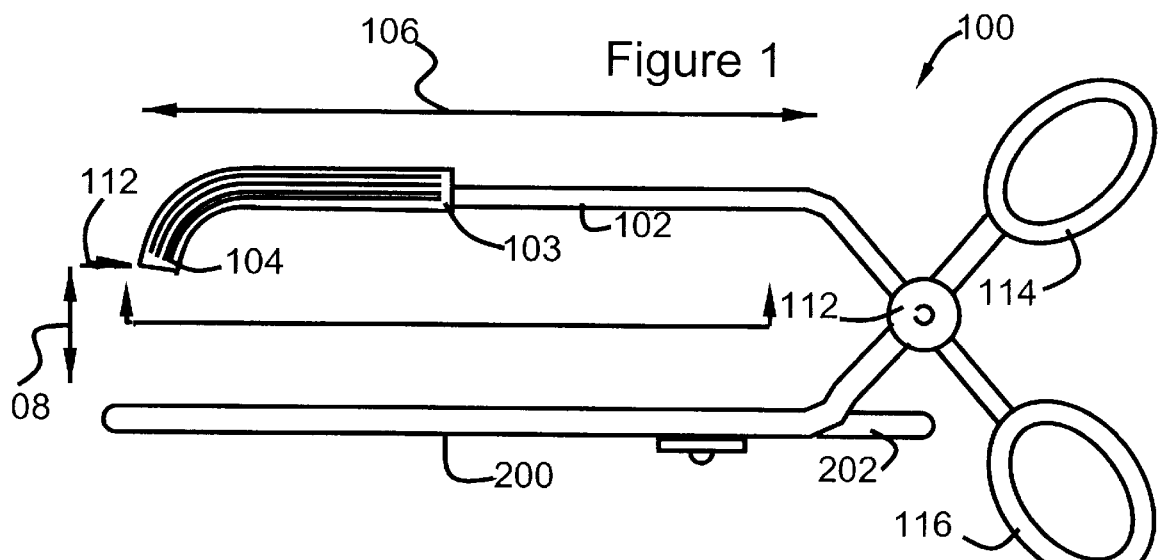
FIG. 1 is a top view of the applicator device of the present invention.

The disclosed placement clamp appliance enables rapid placement of a nasoenteral tube around the nasal septum. The appliance is illustrated in FIG. 1 and indicated generally as 100. The placement clamp appliance 100 is a scissor like device having a fulcrum, or pivot joint, 112 and is operated by inserting the user's fingers into the handles 114 and 116, as typical for using scissors or other pincer like tools. The feed through arm 102 carries, at its distal end, a hollow, tubular guide member 103. The distal end of the tubular guide member 103, is curved medially toward the receiving arm 200, with the opening 104 of the distal end of the tubular member 103 facing the receiving arm 200. Although the preferred curve is at a 90-degree, or slightly less angle, the angle can be slightly greater, although too great an angle will not produce the desired results. The curve of the tubular guide member 103 must be such that it delivers the tube 402 to the receiving arm 200 as illustrated in FIGS. 5–7. Too great an angle and the tube will miss the receiving arm and to small an angle and the tube will be guided down the same nostril. The tubular guide member 103 has an interior diameter that is sufficient to accommodate the small tube that is to serve as a harness. The harness can be a pediatric feed tube, or an equivalent, no greater in size than about 8 French, and having a length of at least about 25 cm.

The receiving arm 200 consists of a pair of clamping members 198 and 204 that rotate around a fulcrum housing 208. The proximal end of the upper clamping member 198 extends beyond that of the lower clamping member 204 to form the handle 114. The configuration of the handles 114 and 116 enable a scissor type movement between the feed through arm 102 and the receiving arm 200. The length of the arm 200 is preferably about one half to one cm. beyond the tubular guide member 103, as indicated by the arrow 112. The extra length facilitates the gripping of the tube and provides a greater margin for error in the event the tube bends or twists away from the proximal end of the appliance 100. The arm 102 and the tubular guide member 103 preferably have a combined straight length, as indicated by arrow 106, of about 12 cm. The mating surfaces of the clamping members 198 and 204 are preferably provided with rough or ridged gripping surfaces 206 to prevent slippage of the tube once grasped. The gripping surfaces 206 can be undulations in the material of manufacture, a coating on the appliance surface or other methods that are known in the medical arts. In the closed position in the position in which the two arms 102 and 200 are closest together, the distal tip 104 of the tubular guide member 103 and the arm 200 are preferably about one cm. apart, as indicated by arrow 108.

Figure 2:
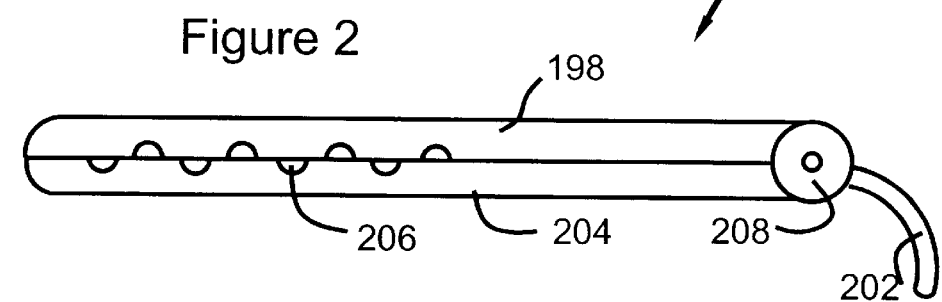
FIG. 2 is a fragmentary side view of the clamp portion of the applicator of FIG. 1, with the clamp biased in the closed position.

The receiving arm 200, illustrated in FIG. 2, is formed from a portion of the upper clamping member 198 and lower clamping member 204. The upper clamping member 198 extends beyond the lower clamping member 204 to form the handle 114. The upper clamping member 198 and lower clamping member 204 are biased toward the clamped position through the use of a coil spring, or other tension producing member, positioned within the fulcrum housing 208. In the illustrated embodiment, the lower clamping arm 204 is moved away from the upper clamping arm 198 by a lever 202. The action of the lever 202 can be countered by holding the handles or, alternatively the upper arm 198 can be provided with a counter lever. This is one method of separating the clamping members 198 and 204 and other methods will be evident to those skilled in the art.

Although the illustrated embodiment shows the lower clamping arm 204 on, what in relation to the diagram of FIG. 1, is the under part of the appliance 100, the appliance can be reversed and still be effective. The criticality lies in the scissor action between the feed through fit arm 102 and the receiving arm on one plane and the scissor action between the lower clamping arm 204 and the upper clamping arm 198 on a second plane. The first and second planes must be at approximately right angles to one another to enable the transfer of the tube 402 between the feed through arm 102 and the receiving arm 200.

Figure 3A:
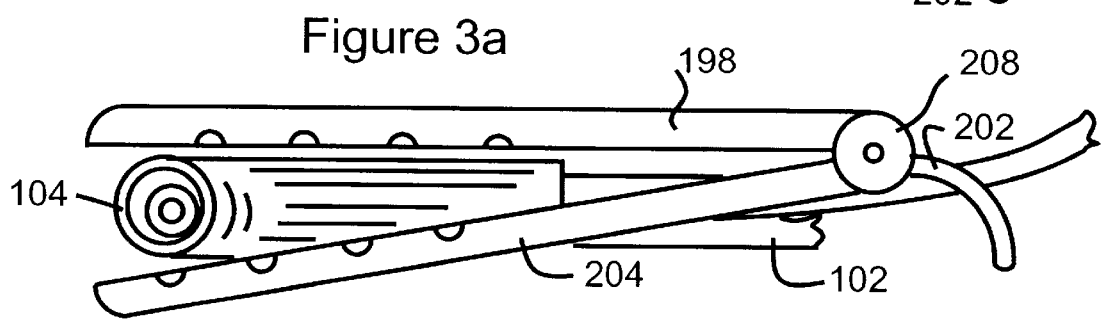
FIGS. 3a is a fragmentary side view of the tubular guide and clamp portion of the applicator of FIG. 1, with the clamp in the open position.
Figure 3B:
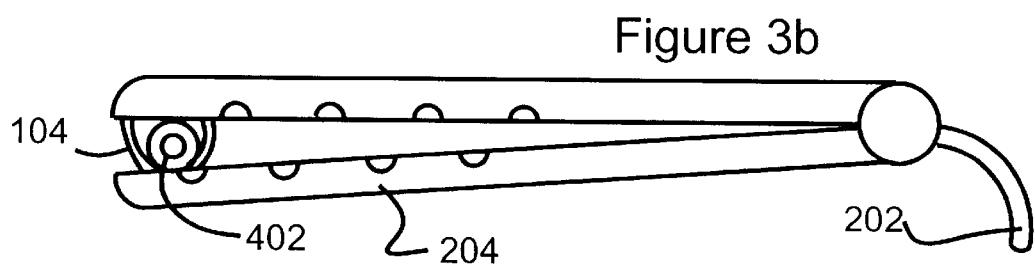
FIG. 3b is a fragmentary side view of the tubular guide and clamp portion of the applicator of FIG. 1 showing the clamp held in the closed position and engaging the harness tube.

As illustrated in FIGS. 3a and 3b, the upper clamping arm 198 and lower clamping arm 204 are spread to the open position, by movement of the lever 202, to receive the pediatric tube 402. Once the tube 402 is positioned between the separated clamping arms 198 and 204, the lever 202 is released and the upper arm 198 and lower arm 204 are returned to their "closed" position. The engagement between the clamping arms 198 and 294 and the pediatric tube 402 is illustrated in FIG. 3b, and also shown in FIG. 4. It should be noted that while reference is made to the harness being formed from a pediatric tube, any inert, flexible tubular or solid member can be employed and the alternate tubing will be evident to those skilled in the medical arts. The harness must be of a sufficient diameter to avoid injuring or irritating the septum and must be sufficiently flexible to readily turn corners, as required. The harness materials disclosed in the '448 patent, are equally usable in the harness of the present invention.

The use of the disclosed appliance 100 is illustrated in FIGS. 5–7. The pediatric tube 402 is inserted into the tubular guide member 103 of the appliance 100 so that the tip of the tube is even with the distal end of the guide member 103. The appliance 100 is inserted into the nasal passages, such that the arms 102 and 200 are in parallel positions, each in one nasal passage. The appliance 100 is inserted until either the tip hits the back wall of the nasopharynx or the fulcrum approaches the columella. The pediatric tube 402 is advanced toward the receiving arm 200 and, as the opening 104 of the tubular guide member 103 is curved toward the receiving arm 200, the tube 402 progressed in the direction of the open receiving arm 200. Once the tube 402 has progressed slightly past the receiving arm 200, as illustrated in FIG. 6, it is secured by the closure of the upper arm 198 and lower arm 204. The appliance 100 is slowly withdrawn from the nasal passages, as illustrated in FIG. 7, with the pediatric tube 402 resting against the distal edge 504 of the septum 502. The pediatric tube 402 is continually advanced, in the direction of the arrow 800, during the withdrawal step until, as illustrated in FIG. 8, the appliance 100 is total out of the nasal passages, and the distal end of the pediatric tube extends beyond the columella 802.

Figure 9:
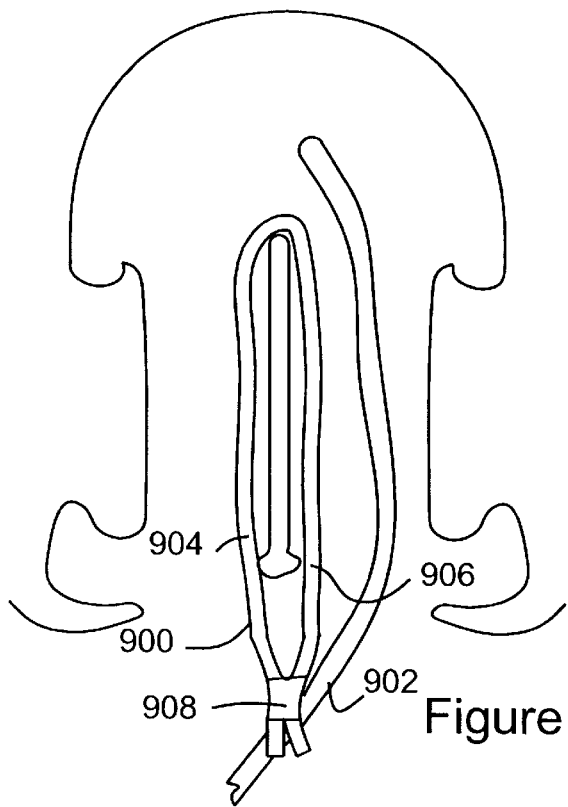
FIG. 9 is a schematic view of the nasogastric tube in place and the harness tied off and trimmed.

The proximal end and any excess distal end of the pediatric tube 402 are cut so that the tube 402 is of the minimum desired length, advantageously a few centimeters from the nasal passages on either side. The tube 402 is the formed into a harness 900, illustrated in FIG. 9, by securing the distal end 904 and proximal end 906 at the closure point 908. The closure point 908 can be formed by tying together 0-silk or similar suture, plastic closures or other means known in the art. The nasogastric tube 902 is secured to the harness 900 through ties, clasps or other known methods.

Figure 10:
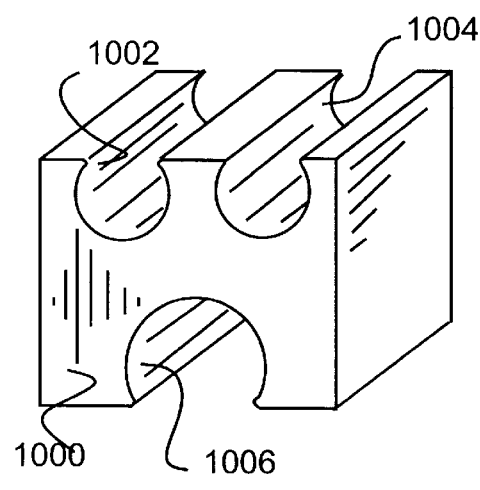
FIG. 10 is a perspective view of a clamp element for use in securing the harness ends and the harness to the nasogastric tube.
Figure 11:
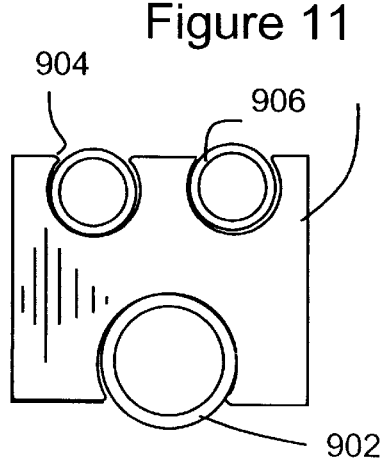
FIG. 11 is an end view of the clamp element of FIG. 10, with the harness and nasogastric tube clamped in place.
Figure 12:
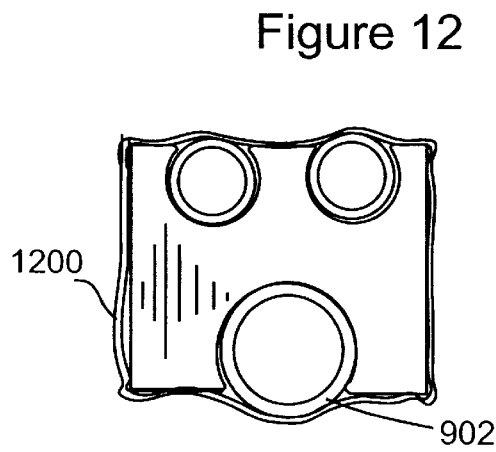
FIG. 12 is an end view of the clamp element of FIG. 11, with the harness and nasogastric tube clamped in place and having an overlay of tape.

Rather than tying the tubing to form the harness 900, a plastic retaining device 1000, as illustrated in FIGS. 10–12, can be used. The retaining device is provided with a pair of grooves 1002 and 1004 for receiving the harness distal end 904 and proximal end 906 respectively. A third groove 1006 is provided to receive the nasogastric tube 902. The assembly can be wrapped in a tape 1200, as illustrated in FIG. 12, to complete the process and prevent slippage.

It is thus seen, that the result is as illustrated in FIG. 2N or 2O of the U.S. Pat. No. 4,778,448 and the U.S. Pat. No. 4,634,425 patents. However, far fewer steps are required to arriving at the final harness structure and the harness assembly is not brought into proximity with the hypopharynx or the pharynx, as required in the system of the '425 patent. Additionally, the harness of the '425 patent must have ends interconnected to form a loop. This step is illustrated in the '425 patent in FIGS. 2E and 2G, in which it is seen that ends 6 and 7 are joined at 30 to form a loop. The juncture region 30 rests against the nasal septum and thus must not have sharp or jagged or otherwise irritating surfaces. Additionally, the juncture must be sufficiently secure to resist coming apart, if a force when a force is applied to the harness, as for example, when the patient pulls on the nasogastric tube. The elimination of the need for interconnecting ends to form a loop totally obviates this problem.

What is claimed is:

1. A method of insertion of a tube around the nasal septum of a patient to form a harness, comprising the steps of:
   inserting a tubular guide into a first nasal passage of a patient,
   feeding a first end of said tube through said tubular guide,
   directing said first end of said tube through an open end of said tubular guide and around said nasal septum,
   clamping said tube proximate said first end and drawing said tube through said tubular guide around said nasal septum and out through a second nasal passage of said patient.

2. The method of claim 1, further comprising the step of removably affixing a first region of said tube proximate said first end of said tube to a second region of said tube proximate said second end of said tube to form a harness.

3. The method of claim 2 further comprising the step of affixing said first region and said second region by tying said first region and said second region with a medically approved material.

4. The method of claim 2 further comprising the step of affixing said first region and said second region with a retaining device, said retaining device having a first end and a second end and multiple slots, each of said multiple slots extending from said first end to said second end, at least two of said slots being dimensioned to retain said harness and at least a third of said slots being dimensioned to receive medical tubing.

5. The method of claim 2, further comprising the step of securing a medical tube, inserted into a patient's body through a nasal passage, to said harness.

6. The method of claim 2 further comprising the step of affixing said first region and said second region with clamp.

7. The method of claim 1, further comprising the step of directing said first end toward a second nasal passage, around said nasal septum, through a curved end of said tubular guide.

8. An appliance for the insertion of a tube around the nasal septum of a patient to form a harness, said appliance having:
   a feed through arm, said feed through arm having:
      a first end and a second end, said first end being a first handle member;

said feed through arm having a tubular guide at said second end, said tubular guide having a curved end, said curved end being distal relative to said first handle member;

a clamping member, said clamp member having an upper clamp arm, a lower clamp arm and a second handle member;

said upper clamp arm being moveable relative to said lower clamp arm in a substantially scissor type action.

9. The appliance of claim 8 further comprising gripping members, said gripping members being along adjacent surfaces of said upper clamping arm and said lower clamping arm and being distal relative to said second handle member.

10. The appliance of claim 8 further comprising a spring member, said spring member biasing said lower clamping member toward said upper clamping member.

11. The appliance of claim 10 wherein said feed through arm and said tubular guide member and said receiving arm have a length sufficient to place said distal end of said tubular guide member and said receiving arm second end past said nasal septum.

12. The appliance of claim 11 wherein said tube is maintained between said upper clamping member and said lower clamping member during withdrawal of said appliance.

13. The appliance of claim 12 wherein said tube is secured by tying said first end and said second end together with a medically approved material.

14. The appliance of claim 12 wherein said tube is secured with a retaining device, said retaining device having a first end and a second end and multiple slots, each of said multiple slots extending from said first end to said second end, at least two of said slots being dimensioned to retain said harness and at least a third of said slots being dimensioned to receive medical tubing.

15. The appliance of claim 10 wherein said tube is secured below a patient's columella.

16. The appliance of claim 10 wherein said harness serves as a securing point for a medical tube inserted into a patient's body through a nasal passage.

17. An appliance for the insertion of a tube around the nasal septum of a patient to form a harness, said appliance having:

a feed through arm, said feed through arm having a first end and a second end, said first end being angled to form a first handle member;

a tubular guide member, said tubular guide member being a hollow member at said feed through arm second end and having an approximately 90 degree curve at said guide member distal end, a receiving arm, said receiving arm having a first end and a second end to form a length, said first end being angled to form a second handle member;

a handle pivot, said handle pivot forming a swivel juncture between said receiving arm and said feed through arm to enable said receiving arm handle and said feed through arm handle to move relative to one another in a scissor action along a first plane;

an upper clamping member, said upper clamping member being formed from a portion of said receiving arm length;

a fulcrum housing, said fulcrum housing forming a swivel juncture and being adjacent to a proximal end of said upper clamping member;

a lower clamping member, said lower clamping member extending from said fulcrum housing to said receiving arm second end and being moveable in relation to said upper clamping member, said lower clamping member able to pivot relative to said upper clamping member along a second plane;

a spring member, said spring member being within said fulcrum housing to bias said lower clamping member adjacent said upper clamping member;

a handle member, said handle member being affixed to said lower clamping arm to enable user movement of said lower clamping arm relative to said upper clamping arm;

gripping members, said gripping members being along adjacent surfaces of said upper clamping arm and said lower clamping arm;

wherein the movement of said handles causes said feed through arm and said receiving arm to move relative to one another on a first plane and movement of said handle member causes said upper clamping member and said lower clamping member to move relative to one another on a second plane.

18. The appliance of claim 17 wherein said distal end of said tubular guide member directs a tube, passed along said feed through arm and said tubular guide member, to be received by said receiving arm, wherein said upper clamping member and said lower clamping member secure said tube.

* * * * *